United States Patent [19]

Kuhl et al.

[11] Patent Number: 5,670,332
[45] Date of Patent: Sep. 23, 1997

[54] ENZYMATIC REACTIONS AND APPARATUS FOR CARRYING THEM OUT

[75] Inventors: Peter Kuhl, Eilengburg; Uwe Eichhorn, Grosserkmannsdorf; Hans-Dieter Jakubke, Leipzig; Karlheinz Drauz, Freigericht; Andreas Bommarius, Frankfurt, all of Germany

[73] Assignee: Degussa Aktiengesellschaft, Frankfurt am Main, Germany

[21] Appl. No.: 312,674

[22] Filed: Sep. 28, 1994

Related U.S. Application Data

[63] Continuation of Ser. No. 52,928, Apr. 27, 1993, abandoned.

[30] Foreign Application Priority Data

Apr. 29, 1992 [DE] Germany ............... 42 14 157.5

[51] Int. Cl.$^6$ ................................. C12N 21/00
[52] U.S. Cl. ............... 435/68.1; 435/173.1; 435/183; 435/219
[58] Field of Search ............... 435/68.1, 173.1, 435/183, 219

[56] References Cited

FOREIGN PATENT DOCUMENTS

| | | |
|---|---|---|
| 271584 | 9/1991 | Czech Rep. . |
| 93 106333 | 9/1994 | European Pat. Off. . |
| 0106146 | 4/1984 | Germany . |
| 0137688 | 3/1985 | United Kingdom . |

OTHER PUBLICATIONS

Kuhl, P., et al., Pharmazie 46:53 (1991).
C. H. Wong and K. T. Wang, "New Developments in Enzymatic Peptide Synthesis," Experientia, Dec. 1991, pp. 1123–1129.
"Biotechnology Techniques" vol. 6, No. 2 Mar./Apr. 1992 pp. 155–160.
Fulcrand-Rolland, et al., Biomed Biochim Acta 50:S213–S216 (1991).
Kuhl, P. et al., BBA 1078:326–8 (1991).

*Primary Examiner*—Blaine Lankford
*Attorney, Agent, or Firm*—Cushman Darby & Cushman IP Group of Pillsbury Madison & Sutro LLP

[57] ABSTRACT

A water-supported enzymatic reaction is carried out with the substrate and the enzyme present in the solid phase. Either the water does not form a liquid continuum around substrate and enzyme, or the water acts at least partially out of the gas phase, or the water required for the reaction is added via a solid, or at least a part of the water required for the reaction is transferred by means of solid body contacts or by a combination of these means. The reaction mixture can be mixed by ultrasound or turbulence, e.g. in a fluidized bed, or both.

9 Claims, 1 Drawing Sheet

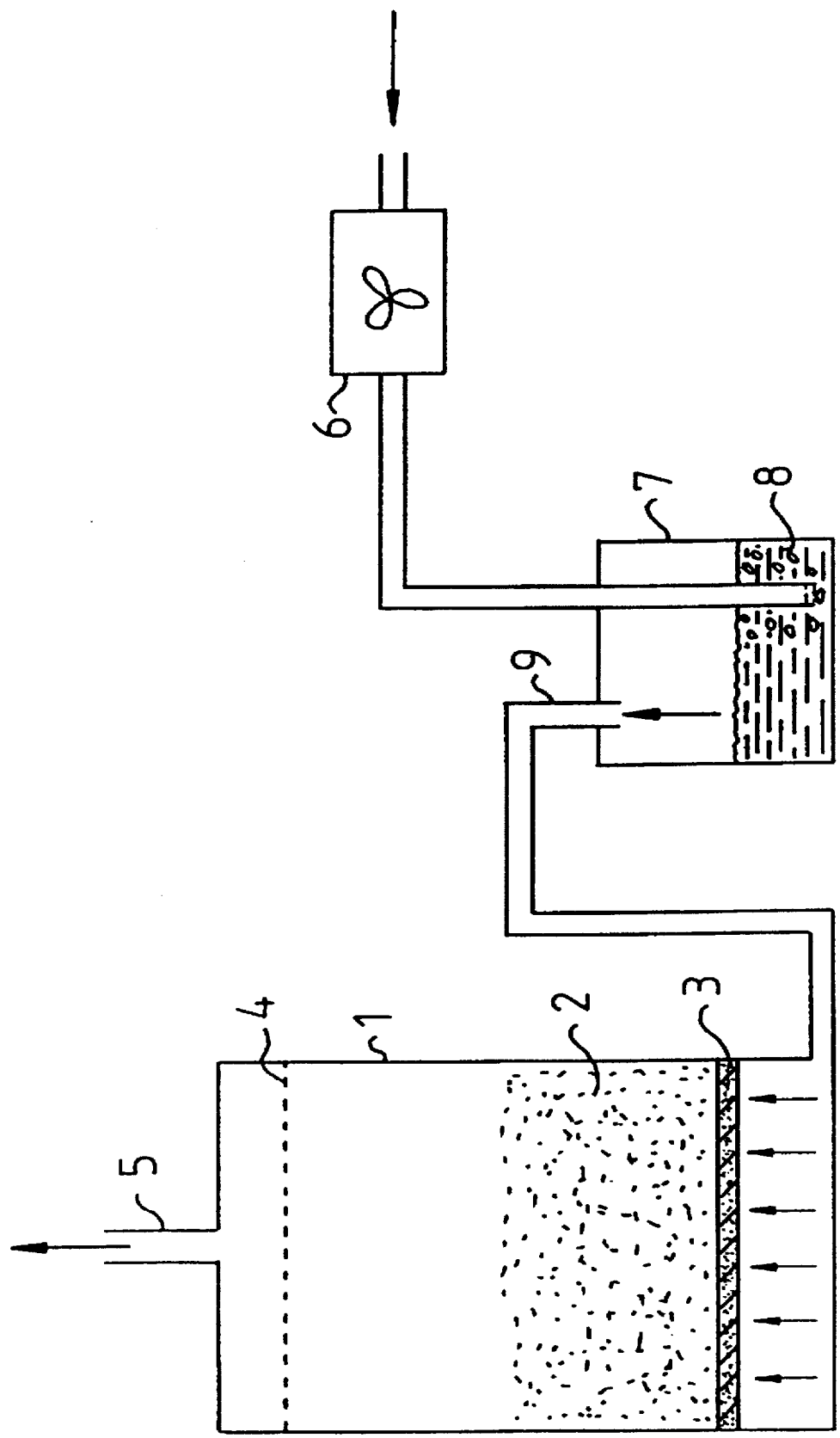

5,670,332

ENZYMATIC REACTIONS AND APPARATUS FOR CARRYING THEM OUT

This is a continuation of application No. 08/052,928, filed on Apr. 27, 1993, which was abandoned upon the filing hereof.

The invention relates to water-supported enzymatic reactions between a substrate and an enzyme as well as to apparatus for carrying out an enzymatic reaction.

The method of the invention is preferably used in reactions which cannot be carried out or are carried out only poorly in aqueous systems because of hydrolysis of the educts or on account of an unfavorable state of an equilibrium involving water.

BACKGROUND OF THE INVENTION

Enzymatic reactions are basically water-supported, i.e., a substrate and an enzyme require water in order to be able to react with one another. Enzymatic reactions of this type can be conversions of a single substrate or of several substrates using a single enzyme or several enzymes, and additional substances, such as, e.g., cofactors, can also be present. Thus, in the description which follows, the term "substrate" refers to an educt which is converted to the desired product.

Reaction systems are already known in which the water content is reduced in order to minimize reactions of hydrolysis or to shift the equilibrium in the direction of the side of the reaction equation containing water. Thus, for example, organic solvents are used to which more or less water is supplied, depending on the solubility (see e.g.: A. M. Klibanov, Trends in Biochem. Sci. 1989, vol. 14, 141–44). Enzymatic reactions have also been carried out in inverse micellar media (J. W. Shield, H. D. Ferguson, A. S. Bommarius and T. A. Hatton, Ind. Eng. Chem. 1986, vol. 25, 603–12).

Furthermore, reactions have been carried out in the gas phase, e.g. with gaseous alcohols as the substrate (E. Banzana, M. Karel and A. M. Klibanov, Biotech. Bioeng. 1989, vol. 34, 1178–85; S. Pulvin, F. Parvaresh, D. Thomas and M. D. Legoy, Ann. N.Y. Acad. Sciu. 1988 Vol. 542, 434–9) or with gas forming esters and alcohols for transesterification (F. Parvaresh, H. Robert, D. Thoms and M. D. Legay, Biothech. Bioeng. 1992, vol. 39, 467–73).

Cofactors were used in some cases, in addition to the immobilized enzyme, in the above-mentioned reactions. The cofactors were not regenerated and/or were immobilized on solid carriers which were saturated with water under a partial pressure.

Enzymatic reactions in an organic solvent have the disadvantage that interactions frequently occur between the enzyme and the organic solvent. These interactions between the organic solvent and the enzyme frequently result in changes in the structure of the enzyme with unfavorable effects on its stability and activity, which adversely affects the formation of peptide-bonds linkage in peptide synthesis reactions (JAKUBKE, H.-D., KUHL, P., KONNECKE, A.: Angew. Chem. 97, 79–87 (1985); Angew. Chem. Int. Ed. Engl. 24, 85 (1985); JAKUBKE, H.-D., in: "The Peptides: Analysis, Synthesis, Biology" (UDENFRIEND, S., MEIENHOFER, J., Eds.) Academic Press, New York (1987), 103–165; KULLMANN, W.: "Enzymatic Peptide Syntheses", CRC Press, Boca Raton (1987); JAKUBKE, H.-D., Kontakte 1991 (3), 60; ibid. 1992 (1), 46).

Reactions in the gas phase are difficult to control and, moreover, as in the case of organic solvents, the gaseous substrate can enter into detrimental interactions with the enzyme. For this reason such enzyme reactions are useful for only a few substrates and enzymes. They can usually not be carried out on an industrial scale.

Reactions in the solid phase have also become known recently in which the substrate and the enzyme are pulverized [powdered, triturated] in the presence of $Na_2CO_3 \cdot 10H_2O$. The water of hydration in the salt supplies the reaction mixture with the required amount of water. The mixing is carried out in a homogenizer. A scale-up of the reaction is doubtful, since the possibility of intimate mixing with a homogenizer can no longer be assumed to take place. In addition, depending on the synthesis, the presence of high concentrations of salt can be undesirable, and the success of the workup after the reaction doubtful.

SUMMARY OF THE INVENTION

The object of the present invention is to provide an enzymatic method which can be carried out as universally as possible for the production of products in which hydrolytic side reactions, organic solvents and, if desired, also high concentrations of salt can be largely avoided. A further object is to provide such a method which can make possible a simplified and environmentally more acceptable process.

These and other objects are accomplished in a water-supported enzymatic reaction between a substrate and an enzyme in which the substrate and the enzyme are present in solid phase and the water does not form a liquid continuum between substrate and enzyme and/or in which the substrate and the enzyme are present in solid phase and the water acts at least partially out of the gas phase and/or in which the substrate and the enzyme are present in solid phase and the water required for the reaction is added via a solid and/or in which the substrate and the enzyme are present in the solid phase and at least a part of the water required for the reaction is transferred by solid contact. An important feature of one embodiment of the process is that the components are intimately mixed by the application of ultrasound.

A common feature of all these measures is the fact that the substrate and the enzyme are present in a solid phase. In addition, the process is carried out, to the extent possible, with a minimum amount of water. The amount of water is such that only enzymatic activity occurs, but that any side reactions such as hydrolysis are largely suppressed. As a rule, organic solvents can be eliminated by this means. Given such a small amount of water, the enzyme and the substrate are not dissolved but rather only hydrated, so that they must be brought into contact with each other as a solid. In the case of conventional enzymatic reactions, at least one reactant, usually the substrate, is in a fluid phase, that is, liquid or gaseous phase, so that the contact necessary for carrying out the reaction is provided solely by the convection motion of the liquid phase.

In the present case the substrate-enzyme mixture is moved mechanically because of the lack of a fluid phase and the substrate and the enzyme are brought into intimate contact with each other. This motion is achieved, depending on the method, by applying ultrasound (sufficient energy) or by whirling up by passing a gas through the solids. In the latter case, a fluidized bed is preferred.

Enzymatic conversions in which moist air is passed through a substrate and, if applicable, a fluidized bed is produced, are known from solid fermentations (e.g. Published German Patent Application DE-A 32 37 896 and "Forum Mikrobiologie" 9/88, pp. 386–394). Solid fermentation, which exhibits advantages in a few microbiological processes over "stirred tank fermentation", requires large amounts of air and moisture in order, on the one hand, to keep the microbiological processes operating and, on the other hand, to carry off the heat produced. Enzymes can also be given off from the microorganisms to the substrate in the microbiological processes. These extracellular enzymes, e.g. proteases, exhibit the same enzymatic activity as in solution and break down peptides to amino acids. This enzymatic activity even remains when the supplied amount of water is so longer sufficient to maintain the microbiological process.

In contrast to that process, the present enzymatic reaction does not involve microbiological processes in which microorganisms must be supplied with air and moisture but rather concerns enzymatic conversions without the cooperation of microorganisms. If, according to the present invention, the yield in the enzymatic reaction is susceptible of being reduced by hydrolysis of a reactant, moisture in the passed-through gas is adjusted so that the enzymatic reaction of the invention and not hydrolysis is favored. This is in distinction to solid fermentation, in which the moisture content of the substrate is approximately 70% and a resulting moisture loss is compensated by moist air having 90–97% relative moisture.

Since the present reactions require a minimum amount of water, the reaction can be characterized by various features. They are:
1. The water does not form a liquid continuum between substrate and enzyme.
2. The water can act at least partially from the gas phase.
3. The water required for the reaction can be added to the reaction via a solid.
4. The water required for the reaction can either be transferred from a solid to the substrate and/or enzyme or can be transferred between substrate and enzyme by solid contacts.

Feature 1 has the advantage that very small amounts of water can be used, so that e.g. hydrolytic side reactions are avoided. Moreover, it is possible to eliminate organic solvents which have generally been used to dilute or replace the liquid water continuum used in conventional enzymatic reactions in order to likewise reduce the amount of water. Feature 2 also has the advantage that very small amounts of water can be used. The water present in small amount passes partially into the gas phase so that it is available from there for the reaction. The water can also be supplied with advantage to the reaction from the gas phase. Features 3 and 4 have the advantage that the water can be supplied to the reaction in a well-controlled manner by means of the conditioning of a solid, e.g. a zeolite, or by means of the conditioning of substrate and/or enzyme.

These features can be used individually or in combination for the reaction of the invention and in particular, Feature 1 can be combined with the others of the points enumerated above.

The invention can eliminate damage to the enzyme which is otherwise possible in enzymatic peptide syntheses when organic cosolvents, miscible or non-miscible with water, are added. The invention also eliminates the reduction of the catalytic activity associated therewith. Moreover, the hydrolytic side reactions of reactant and product, which adversely affect the effectiveness of the synthesis, can be considerably reduced by the use, in accordance with the invention, of reaction systems with a minimum water content.

Additives of organic solvents and/or buffer solutions can usually be eliminated if sufficient contact of the reactants and of the catalytically active enzyme is assured.

The method of the invention is especially effective where larger amounts of water adversely influence the enzymatic reaction. In these instances, and in accordance with the invention, the amount of water is essentially reduced to the level that preferably only the enzymatic activity is still observed. The side reactions can be retarded sufficiently in this way that they can be essentially disregarded. The method then provides at least one of Features 1 to 4.

When several substrates react to a final product, it is preferable if all substrates, are solid. Since enzymatic hydrolyses do not as a rule demonstrate the problems cited above, the method of the invention is particularly useful in non-hydrolytic reactions.

Since enzymatic reactions are usually disturbed, as mentioned above, by organic solvents, it is advantageous according to the invention if the amount of water is reduced to the point where organic solvents can be eliminated. However, it can be required or advantageous if small amounts of solvent are still present. These solvent amounts should be used in less than equimolar amounts relative to the water, especially if they can dissolve the water present.

The method of the invention is especially useful for condensation reactions, since, in these reactions, a large amount of water usually shifts the equilibrium in such a manner that the reaction yield is adversely affected. In particular, the method of the invention is useful for condensation reactions used in peptide syntheses, since the method of the invention makes especially mild conditions available for them.

An especially preferred method in which the solids participating in the method are whirled up by introducing a gas is preferably carried out in a fluidized bed chamber with a bottom which is permeable to gas but which retains a substrate-enzyme mixture, and which includes means for introducing gas through the gas-permeable bottom, and means for maintaining the moisture content of a substrate-enzyme mixture located in the fluidized bed chamber, within a predetermined range.

The apparatus contains a chamber which is suitable for receiving the substrates and enzymes used. The bottom of the chamber should be permeable to gas, but it retains the solid substances described above. A gas can be introduced through the chamber bottom, which bottom is designed so that, upon a certain gas flow through the bottom, the solid substances in the chamber are converted into a fluidized bed. Moreover, the apparatus also requires means for maintaining the moisture in the fluidized bed and in the substrate-enzyme mixture within a predetermined range so that the enzymatic reaction is assured and any side reactions are suppressed. Given too low a moisture content, no enzymatic reaction can take place. Conversely, if the moisture content is elevated above a certain value, side reactions increase, if applicable, and/or the solid substances adhere, so that the fluidized bed collapses.

It is preferable, in a device of the type described, if the moisture is supplied via the gas introduced through the gas-permeable bottom, in which instance the moisture control in the fluidized bed can be achieved by adding water (vapor) to the gas to be introduced. This loading of the gas can be achieved e.g. by passing the gas through water or an aqueous salt [saline] solution, e.g. 5% sodium hydrogen carbonate solution, bypassing the gas over salt hydrates, e.g. calcium chloride hexahydrate or by other known moisture conditioning methods.

BRIEF DESCRIPTION OF FIGURE OF DRAWING

The drawing shows an apparatus for carrying out the invention schematically.

DETAILED DESCRIPTION OF PREFERRED EMBODIMENT

One form of apparatus useful in carrying out the invention will be described in more detail, reference being made to the drawing.

In the drawing, a substrate-enzyme mixture 2, for instance of the type described in Examples 4 and 5, is present in a fluidized bed 1. Fluidized bed chamber 1 is closed at its lower end by bottom 3, which is gas-permeable but which retains substrate-enzyme mixture 2. Suitable bottoms of this type are e.g. frits of glass or of metal. The upper end of the fluidized bed chamber contains sieve 4 which is intended to retain solid particles of the substrate-enzyme mixture which have whirled up too far. Opening 5 is provided above safety sieve 4 in fluidized bed chamber 1, through which opening a gas conducted through fluidized bed chamber 1 (arrows) can exit. A suitable gas is e.g. air or nitrogen.

The gas is introduced via controllable pump 6 and conducted into liquid 8 located in container 7. Liquid 8 consists of a 5% sodium hydrogen carbonate solution in water. Instead of pump 6, a pressure cylinder with the carrier gas can also be connected directly to container 7.

The gas exits container 7 via outlet 9, which is located sufficiently above liquid 8, and is conducted below bottom 3 into fluidized bed chamber 1.

Depending on the speed of the gas flowing through bottom 3, a state is achieved in the substrate-enzyme mixture, which should be present as a loose [bulk] material which is as fine as possible, which state resembles that of a boiling liquid. Depending on the conditions employed (substrate, enzyme, water content, temperature, etc.), substrate-enzyme mixture 2 is maintained for a certain time in this state and the reaction is subsequently terminated. During the reaction, the substrate-enzyme mixture is converted at least partially into a product-enzyme mixture. The product is isolated to the extent desired with conventional methods from this product-enzyme mixture.

EXAMPLES

In the examples which follow, the amino acids and peptides are abbreviated in accordance with the internationally accepted rules. The ultrasound conditions were as follows: 35 kHz, 50 W; device USG 50 (Messgeratewerk Ballenstedt) Examples using ultrasound

Example 1

Synthesis of Z-Phe-Leu-$NH_2$ 30 mg (0.1 mole) Z-Phe-OH and 13 mg (0.1 mmole) Leu-$NH_2$ are placed into an unsealed glass container having a 12 mm inner diameter and stirred with a spatula. Then, a mixture of 161 mg (0.5 mole) $Na_2SO_4.10H_2O$ and 5 mg thermolysine is added, the glass container is closed and subjected to ultrasonic waves in an ultrasound bath at 40° C. After 20 minutes the reaction is stopped with 0.4 ml 5% (v/v) aqueous trifluoroacetic acid. The analytical evaluation is carried out by means of HPLC and comparison with an authentic specimen.

Yield: 87% of theory

Example 2

Synthesis of Ac-Gly-Trp-Leu-$NH_2$

The procedure of Example 1 is repeated except that 30.3 mg (0.1 mole) Ac-Gly-Trp-OH are used as the carbon component.

Yield: 79% of theory

Example 3

Synthesis of Z-Asp-Phe-OMe 26.7 mg (0.1 mmole) Z-Asp-OH, 20.3 mg (0.1 mmole) Phe-O.HCl and 28.6 mg (0.1 mmole) $Na_2CO_3.10H_2O$ are placed into the glass container and intermixed in a manner which is analogous to Example 1. The mixture is then combined with 12.6 mg (0.1 mole) $Na_2SO_4$ and 5 mg thermolysine. After 30 minutes ultrasonic treatment at 40° C. the reaction is stopped and evaluated with HPLC.

Yield 32% of theory

EXAMPLES USING COMPRESSED AIR

Example 4

Synthesis of Z-Ala-Phe-Leu-$HN_2$ 38.5 mg (0.1 mmole) Z-Ala-Phe-OMe, 26.0 mg (0.2 mmole) Leu-$NH_2$ and 10.0 mg (0.4 μmole) chymotrypsin are placed in a 130 mm×20 mm glass tube provided with a frit bottom and whose lower end is drawn out to a tip. Compressed air which had previously been passed through a 5% solution of $NaHCO_3$ was supplied from below in such a manner that the solids located on the frit are whirled up in a straight manner. In addition, the reaction container is moved on an agitator. The reaction time is 3 hours. The reaction mixture is subsequently taken up in 7 ml methanol, filtered and analyzed with HPLC.

Yield: 46% of theory

Example 5

Synthesis of Boc-Ala-Phe-Leu-$NH_2$

In a manner analogous to Example 1, 22% Boc-Ala-Phe-Leu-$NH_2$ are obtained starting with 35.0 mg (0.1 mmole) Boc-Ala-Phe-OMe.

What is claimed is:

1. A process involving a water-supported enzymatic reaction for the synthesis of a peptide comprising, forming a solid phase mixture consisting essentially of a substrate, water and a non-immobilized enzyme suitable for the synthesis of the peptide, subjecting the solid phase mixture to conditions suitable for enzymatic activity and intimately mixing the components by the application of ultrasound wherein water is present as a gas or solid and in an amount that is insufficient to form a liquid continuum between substrate and the enzyme but is sufficient for the enzymatic reaction for the synthesis of a peptide to occur.

2. A process involving a water-supported enzymatic reaction as set forth in claim 1 in which the reaction is not a hydrolysis.

3. A process involving a water-supported enzymatic reaction as set forth in claim 1 in which the substrate, enzyme and water are intimately mixed with each other during the reaction by introducing a gas.

4. A process involving a water-supported enzymatic reaction for the synthesis of a peptide comprising, forming a solid phase mixture consisting essentially of a substrate, water and a non-immobilized enzyme suitable for the synthesis of the peptide, subjecting the solid phase mixture to conditions suitable for enzymatic activity and introducing gas under conditions which cause the components of said mixture to intermix wherein water is present as a gas or solid in an amount that is insufficient to form a liquid continuum between substrate and the enzyme but is sufficient for the enzymatic reaction for the synthesis of the peptide to occur.

5. A process involving a water supported enzymatic reaction as set forth in claim 4 in which ultrasound is applied to the components of said mixture while they are subjected to the introduction of gas.

6. A process involving a water-supported enzymatic reaction as set forth in claim 4 in which at least part of the water required for the reaction is supplied with the gas.

7. A process involving a water-supported enzymatic reaction as set forth in claim 1 or claim 4 in which organic solvents are not used or are used in less than equimolar amounts with respect amount in comparison to the amount of water.

8. A process involving a water-supported enzymatic reaction as set forth in claim 1 or claim 4 in which the reaction is a condensation.

9. A process involving a water-supported enzymatic reaction as set forth in claim 4 or claim 5 in which the reaction is carried out in an apparatus comprising a fluidized bed chamber having a bottom which is permeable to gas but which is constructed and arranged to retain a substrate-enzyme mixture, means for introducing gas through a gas-permeable bottom, and means for maintaining the moisture of a substrate-enzyme mixture located in the fluidized bed chamber within a preselected range.

* * * * *